United States Patent
Mamedov et al.

(10) Patent No.: US 6,235,678 B1
(45) Date of Patent: May 22, 2001

(54) CATALYST SYSTEM FOR OXIDATIVE DEHYDROGENATION OF PARAFFINS

(75) Inventors: Edouard A. Mamedov; Shahid N. Shaikh, both of Houston, TX (US)

(73) Assignee: Saudi Basic Industries Corporation (SA)

( * ) Notice: Subject to any disclaimer, the term of this patent is extended or adjusted under 35 U.S.C. 154(b) by 0 days.

(21) Appl. No.: 09/330,690

(22) Filed: Jun. 11, 1999

(51) Int. Cl.[7] .............................. B01J 23/28; B01J 23/02; B01J 23/16; B01J 23/18; B01J 23/22
(52) U.S. Cl. ...................... 502/354; 502/332; 502/335; 502/336; 502/340; 502/341; 502/342; 502/344; 502/353; 502/355
(58) Field of Search .................................. 502/332, 335, 502/336, 340, 341, 342, 344, 353, 354, 355

(56) References Cited

U.S. PATENT DOCUMENTS

| | | |
|---|---|---|
| 3,119,111 | 1/1964 | McDonald et al. |
| 3,502,739 | 3/1970 | Begley et al. |
| 3,745,194 | 7/1973 | Bertus et al. |
| 3,758,609 | 9/1973 | Cichowski |
| 3,801,671 | 4/1974 | Marsheck |
| 3,860,534 | 1/1975 | Harris et al. |
| 3,927,138 | 12/1975 | Walker |
| 4,046,833 | 9/1977 | Hardman |
| 4,131,631 | 12/1978 | Hardman |
| 4,219,671 * | 8/1980 | Slinkard et al. ............ 568/475 |
| 4,255,284 | 3/1981 | Hardman |
| 4,410,450 | 10/1983 | Sasaki et al. ............... 502/22 |
| 4,524,236 | 6/1985 | McCain ...................... 585/658 |
| 4,568,790 | 2/1986 | McCain ...................... 585/658 |
| 4,658,074 | 4/1987 | Bajars et al. ............... 585/380 |
| 4,746,641 | 5/1988 | Guttmann et al. ......... 502/202 |
| 4,774,216 | 9/1988 | Kolts et al. ................ 502/174 |
| 4,777,319 | 10/1988 | Kung et al. ................ 585/624 |
| 4,788,371 | 11/1988 | Imai et al. ................. 585/443 |
| 4,797,381 | 1/1989 | Bartek et al. .............. 502/202 |
| 4,871,706 | 10/1989 | Brazdil, Jr. et al. ........ 502/209 |
| 4,874,738 | 10/1989 | Brazdil, Jr. et al. ........ 502/209 |
| 4,877,764 | 10/1989 | Glaeser et al. ............. 502/209 |
| 4,895,823 | 1/1990 | Kolts et al. ................ 502/226 |
| 4,918,214 | 4/1990 | Brazdil, Jr. et al. ........ 558/319 |
| 4,940,826 | 7/1990 | Font Friede et al. ...... 585/600 |
| 4,973,793 | 11/1990 | McFarland ................ 585/658 |
| 5,008,427 | 4/1991 | Brazdil, Jr. et al. ........ 558/319 |
| 5,036,037 | 7/1991 | Kladnig et al. ............ 502/319 |
| 5,079,207 | 1/1992 | Brazdil et al. ............. 502/205 |
| 5,086,032 | 2/1992 | Mazzocchia et al. ..... 502/315 |
| 5,139,988 | 8/1992 | Sasaki et al. .............. 502/206 |
| 5,220,090 | 6/1993 | Honda et al. .............. 585/654 |
| 5,498,588 | 3/1996 | Brazdil et al. ............. 502/353 |
| 5,686,381 | 11/1997 | Albonetti et al. .......... 502/352 |
| 5,750,760 | 5/1998 | Ushikubo et al. ......... 558/319 |
| 5,772,898 | 6/1998 | Lewis ........................ 210/762 |
| 6,063,728 * | 5/2000 | Hinago et al. ............. 502/300 |

OTHER PUBLICATIONS

Straguzzi, G.I., Bischoff, K. B., Koch, T.A. and Schuit, G.C.A., "Selective Oxidation Catalysts Containing Antimony for the Conversion of 1–Butene to Butadiene", Journal of Catalysis 103, 357–365 (1987), No Month.

Qiu, Feng–Yan, Weng, Lu–Tao, Ruiz, P. and Delmon, B., "Effect of Antimony (IV) Oxide, Bismuth Phosphate and Tin (IV) Oxide on the Catalytic Properties of Compound Oxide Catalysts in the Oxidative Dehydrogenation of n–Butene", Applied Catalysis, 47 (1989) 115–123, Elsevier Science Publishers B.V., Amsterdam—Printed in The Netherlands, No Month.

Teller, R.G., Brazdil, J.F. and Grasselli, R.K., "Phase Cooperation in Oxidation Catalysis", J. Chem Soc., Faraday Trans. 1, 1985, 81, 1693–1704, No Month.

Straguzzi, G.I. and Dismore, P.F., "Use of X–Ray Diffraction as an Analytical Technique for the Synthesis of Inorganic Catalysts", Powder Diffraction, vol. 2, No. 3, Sep. 1987.

Centi, G. And Ferruccio, T., "Oxidation Catalysts Badsed on Antimony Mixed Oxides with Rutile–Type Structures", Catal. Rev.—Sci. Eng., 28(2&3), 165–184 (1986), No Month.

Tianshu, Z. and Hing, P., $FeSbO_4$ semiconductor ceramics: a new material for sensing liquid–petroleum gas; Journal of Materials Science: Materials in Electronics 10 (1999) 509–518, No Month.

\* cited by examiner

*Primary Examiner*—Elizabeth D. Wood
(74) *Attorney, Agent, or Firm*—Akin, Gump, Strauss, Hauer & Feld, L.L.P.

(57) ABSTRACT

A catalyst composition for oxidative dehydrogenation of paraffinic hydrocarbons and other compounds having at least two adjacent carbon atoms each having at least one hydrogen atom. The catalyst composition is represented by the formula $$A_a B_b Sb_c V_d Al_e O_x$$

wherein A is an alkali or alkaline earth metal; B is one or more optional elements selected from zinc, cadmium, lead, nickel, cobalt, iron, chromium, bismuth, gallium, niobium, tin and neodymium; a is 0 to 0.3, b is 0 to 5, c is 0.5 to 10, d is 1, e is 3 to 10, $7 \leq a+b+c+d+e \leq 25$, and x is determined by the valence requirements of the elements present. A process for the oxidative dehydrogenation of paraffins using the catalyst composition.

9 Claims, No Drawings

CATALYST SYSTEM FOR OXIDATIVE DEHYDROGENATION OF PARAFFINS

FIELD OF THE INVENTION

The present invention relates to a catalyst composition for an oxidative dehydrogenation of organic compounds having alkane functionality to organic compounds having alkene functionality. The present invention also relates to a catalytic process for the oxidative dehydrogenation of alkanes to alkenes.

BACKGROUND OF THE INVENTION

Unsaturated alkenes are useful as monomers and comonomers for the formation of commercially valuable polymers. The conversion of lower value saturated hydrocarbons into higher value unsaturated hydrocarbons is economically desirable. Oxidative dehydrogenation of saturated hydrocarbons to form unsaturated hydrocarbons has been accomplished using catalysts in high temperature gas phase reactions.

Numerous catalysts which can be used for the oxidative dehydrogenation of saturated or paraffinic hydrocarbons have been reported. Mixed nickel and tin oxides have been disclosed in U.S. Pat. No. 3,745,194; U.S. Pat. No. 3,801,671; and U.S. Pat. No. 5,086,032. Complex metal oxide catalyst including vanadium and aluminum for oxidative dehydrogenation of hydrocarbons has been disclosed in U.S. Pat. No. 4,046,833.

Catalysts, having crystalline structures, useful for the oxidative dehydrogenation of saturated hydrocarbons to form unsaturated hydrocarbons are known. U.S. Pat. No. 5,772,898 discloses a metallo manganese oxide having a hollandite structure and an intracrystalline pore system.

U. S. Pat. No. 4,777,319 discloses a catalyst for oxidative dehydrogenation of hydrocarbons using metal vanadate compounds which are described as having crystalline structures. U.S. Pat. No. 5,139,988 discloses an iron-antimony containing oxide catalyst in which the iron antimonate is crystalline. U.S. Pat. No. 4,973,793 discloses crystalline catalyst compositions having iron, oxygen and at least one other metallic element. U.S. Pat. No. 4,658,074 also discloses crystalline catalysts having iron, oxygen and at least on other metallic element.

Calcination is commonly used as one step in the process of preparing catalysts useful for oxidative dehydrogenation. U.S. Pat. No. 3,860,534 disclosed high temperature calcinations at 700° C. to 900° C.

A desire still exists in the art to develop catalyst that will promote a high conversion of alkane starting material with high selectivity to an alkene product material of the same carbon number so as to enable the attainment of a high yield of product per pass.

SUMMARY OF THE INVENTION

One embodiment of this invention is a catalyst in an oxide form containing aluminum, vanadium and antimony which is useful for the oxidative dehydrogenation of organic compound having at least two adjacent carbon atoms each having at least one hydrogen atom. The catalyst composition is represented by the formula $A_aB_bSb_cV_dAl_eO_x$ wherein A is an alkali or alkaline earth metal; B is one or more optional elements selected from zinc, cadmium, lead, nickel, cobalt, iron, chromium, bismuth, gallium, niobium, tin and neodymium; and a is 0 to 0.3, b is 0 to 5, c is 0.5 to 10, d is 1, e is 3 to 10, $7 \leq a+b+c+d+e \leq 25$, and x is determined by the valence requirements of the elements present. The catalyst is prepared by a low temperature process with a calcination temperature below about 650° C. The catalyst is prepared by a process comprising at least a step of heating the catalyst to its calcination temperature using a heating velocity of less than 15° C./minute. The catalyst is substantially amorphous, i.e. without any long range lattice order. The preferred catalyst compositions promote a high conversion of alkane starting material with high selectivity to alkene product material of the same number of carbon atoms to enable production yields of up to 30% per reactor pass.

According to one embodiment of the present invention the catalyst can be on a support material. The support material may be an inorganic compound that is substantially free of alumina or aluminum.

The oxidative dehydrogenation process includes a step of contacting an organic compound containing alkane functionality with the catalyst in a reactor, in the presence of an oxygen containing gas, in the gas phase at an elevated temperature for a time sufficient to convert a portion of the organic compound of alkane functionality to an organic compound containing alkene functionality. The oxidative process may be applied to any organic compound having at least two adjacent bonded carbon atoms each having at least one hydrogen atom.

DETAILED DESCRIPTION OF INVENTION

The subject matter of the present invention is an improved catalyst for a process of oxidative dehydrogenation of compounds having at least two adjacent carbon atoms each having at least one hydrogen atom. The oxidative dehydrogenation process converts alkanes to alkenes. The process is applicable to, but not limited to, for example, ethane, propane, butane, isobutane, pentane, isopentane, hexane and ethylbenzene. The oxidative dehydrogenation process may proceed even in the presence of one or more additional functional groups in the compound to be dehydrogenated. The oxidative dehydrogenation process of the present invention is applicable even in the presence of one or more of the following functional groups: nitrile, alkyl halide, ether, ester, aldehyde, ketone, carboxylic acid and alcohol.

The process of the present invention is useful for the oxidative dehydrogenation of compounds which typically contain from 2 to 20 carbon atoms, have a boiling point below about 350° C., and optionally may contain other elements, in addition to carbon and hydrogen, such as halogen, nitrogen and sulphur. Preferred compounds have from 2 to 12 carbon atoms and most preferred compounds have from 2 to 6 carbon atoms.

The oxidative dehydrogenation process is also applicable to the direct dehydrogenation of an alkane to an alkadiene or to the dehydrogenation of an alkene to an alkadiene. For example, the process can convert isopentane to isopentene or convert isopentane, through an isopentene intermediate, to isoprene.

CATALYST COMPOSITION

The catalyst composition is represented by the formula $A_aB_bSb_cV_dAl_eO_x$ wherein A is an alkali or alkaline earth metal; B is one or more optional elements selected from zinc, cadmium, lead, nickel, cobalt, iron, chromium, bismuth, gallium, niobium, tin and neodymium; and a is 0 to 0.3, b is 0 to 5, c is 0.5 to 10, d is 1, e is 3 to 10, $7 \leq a+b+c+d+e \leq 25$, and x is determined by the valence requirements of the elements present.

Catalyst precursors may be prepared by conventional physical methods utilizing mixing, co-precipitation, impregnation and filtration. Preferred starting materials are water soluble metal salts which include, but are not limited to, metal nitrates, chloride, oxalates and hydroxides. For metal salts in which the metal is an anionic ion, an ammonium cation may be used as a counterion.

The catalyst of the present invention can be produced by preparing one or more solutions or slurries, preferable aqueous solutions or slurries, each containing one or more of the starting materials. For example, a slurry of an alumina precipitate is formed by adjusting the pH of an aluminum salt solution with ammonium hydroxide. The remaining solutions or slurries are mixed, with pH adjustment as needed, to form a mixed metal precipitate. The mixed metal precipitate is added to the alumina slurry and the resulting solids are recovered by filtration, dried and calcined in a non-reducing atmosphere to prepare an oxide form of the catalyst.

Some catalysts are further impregnated prior to calcination with one or more Group I and/or Group II elements. A compound of the Group I or Group II element, for example potassium hydroxide, may be dissolved in water and impregnated onto the catalyst by incipient wetness. Typically water that is substantially free of dissolved metals, for example de-ionized water, may be used. Alternatively semiconductor grade water may be used to dissolve the compound of the Group I or Group II element in order to reduce the introduction of contaminating cations which may inhibit the catalyst.

The term "aqueous solution" includes not only a solution in which the solute is completely dissolved but also a slurry in which part or all of the solute is undissolved. The aqueous solution also includes acidic, neutral or basic solutions. For starting materials with limited solubility in a neutral aqueous solution, acid or base may be added to increase the amount of dissolved starting material. Dissolution of starting materials may also be aided by heating the aqueous solutions. Typically the aqueous solutions are heated from about 50° C. to about 90° C.

The concentration of the starting materials in the aqueous solutions may vary broadly. Generally the amount of starting materials in the aqueous solution or slurry ranges from about 5 weight percent to about 60 weight percent of the total weight of the solution or slurry. Typically, the amount of starting material in the solution or slurry is about 10 weight percent to about 30 weight percent.

Typically deionized water is used to prepare the aqueous solutions or slurries. The use of deionized water aids in the reduction of contamination of the catalysts from water borne cations.

The present invention is a catalyst composition of a formula of $A_aB_bSb_cV_dAl_eO_x$, wherein A is an alkali or alkaline earth metal; B is one or more optional elements selected from zinc, cadmium, lead, nickel, cobalt, iron, chromium, bismuth, gallium, niobium, tin and neodymium; and a is 0 to 0.3, b is 0 to 5, c is 0.5 to 10, d is 1, e is 3 to 10, $7 \leq a+b+c+d+e \leq 25$, and x is determined by the valence requirements of the elements present. Preferred catalysts are those wherein a is from about 0.01 to about 0.1, b is from about 0.1 to about 1, c is from about 0.5 to about 3, e is from about 4 to about 7 and x is determined by the valence requirements of the elements present. More preferred catalysts are those wherein B is at least one element selected from the group consisting of zinc, nickel, cobalt, iron, bismuth and niobium.

One embodiment of the present invention is a catalyst composition of a formula consisting essentially of $A_aB_bSb_cV_dAl_eO_x$, wherein A is an alkali or alkaline earth metal; B is one or more optional elements selected from zinc, cadmium, lead, nickel, cobalt, iron, chromium, bismuth, gallium, niobium, tin and neodymium; and a is 0 to 0.3, b is 0 to 5, c is 0.5 to 10, d is 1, e is 3 to 10, $7 \leq a+b+c+d+e \leq 25$, and x is determined by the valence requirements of the elements present. Preferred catalysts are those wherein a is from about 0.01 to about 0.1, b is from about 0.1 to about 1, c is from about 0.5 to about 3, e is from about 4 to about 7 and x is determined by the valence requirements of the elements present. More preferred catalysts are those wherein B is at least one element selected from the group consisting of zinc, nickel, cobalt, iron, bismuth and niobium.

Illustrative catalyst compositions encompassed by the claimed subject matter include, but are not limited to, the following examples:

$Sb_{0.5}V_{1.0}Al_{6.1}$;
$Ni_{0.3}Sb_{0.5}V_{1.0}Al_{6.1}$; $Ni_{0.3}Sb_{1.5}V_{1.0}Al_{6.1}$; $Ni_{0.3}Sb_{3.0}V_{1.0}Al_{6.1}$;
$Fe_{0.3}Sb_{0.5}V_{1.0}Al_{6.1}$; $Fe_{0.3}Sb_{1.5}V_{1.0}Al_{6.1}$; $Fe_{0.3}Sb_{3.0}V_{1.0}Al_{6.1}$;
$Zn_{0.3}Sb_{0.5}V_{1.0}Al_{6.1}$; $Cd_{0.3}Sb_{0.5}V_{1.0}Al_{6.1}$; $Co_{0.3}Sb_{0.5}V_{1.0}Al_{6.1}$;
$Nb_{0.3}Sb_{0.5}V_{1.0}Al_{6.1}$; $Bi_{0.3}Sb_{0.5}V_{1.0}Al_{6.1}$; $Ga_{0.3}Sb_{0.5}V_{1.0}Al_{6.1}$;
$Sn_{0.3}Sb_{0.5}V_{1.0}Al_{6.1}$; $Cr_{0.3}Sb_{0.5}V_{1.0}Al_{6.1}$; $Nb_{0.16}Fe_{0.17}Sb_{0.5}V_{1.0}Al_{6.1}$;
$Cr_{0.16}Fe_{0.17}Sb_{0.5}V_{1.0}Al_{6.1}$; $K_{0.15}Fe_{0.3}Sb_{0.5}V_{1.0}Al_{6.1}$; $K_{0.3}Fe_{0.3}Sb_{0.5}V_{1.0}Al_{6.1}$;
$K_{0.06}Fe_{0.3}Sb_{0.5}V_{1.0}Al_{6.1}$; $K_{0.15}Fe_{0.3}Sb_{0.5}V_{1.0}Al_{6.1}$; $Na_{0.06}Fe_{0.3}Sb_{0.5}V_{1.0}Al_{6.1}$;
$Cs_{0.06}Fe_{0.3}Sb_{0.5}V_{1.0}Al_{6.1}$; $Mg_{0.06}Fe_{0.3}Sb_{0.5}V_{1.0}Al_{6.1}$; $Ba_{0.06}Fe_{0.3}Sb_{0.5}V_{1.0}Al_{6.1}$;
$Na_{0.06}Ni_{0.3}Sb_{0.5}V_{1.0}Al_{6.1}$; $K_{0.06}Ni_{0.3}Sb_{0.5}V_{1.0}Al_{6.1}$; $Cs_{0.06}Ni_{0.3}Sb_{0.5}V_{1.0}Al_{6.1}$;
$Mg_{0.06}Ni_{0.3}Sb_{0.5}V_{1.0}Al_{6.1}$; and $Ba_{0.06}Ni_{0.3}Sb_{0.5}V_{1.0}Al_{6.1}$.

The calcination temperature affects the selectivity and activity of the oxide catalyst. The selectivity and activity of the oxide catalysts decrease with increasing calcination temperature over the range from about 450° C. to about 950° C. Suitable oxide catalysts were prepared using calcination temperatures below about 700° C. Preferred calcination temperatures are from about 450° C. to about 650° C.

The elevating temperature velocity or heat-up rate during calcination also affects catalyst properties such as phase composition, attrition resistance, surface area and particle size. Acceptable catalyst may be prepared with a heat-up rate of from about 5° C. to about 30° C./minute. A preferred heat-up rate is from about 10° C./minute to about 20° C./minute. A more preferred heat up rate is from about 5° C./minute to about 10° C./minute. The heating rate may be varied to modify the surface area of the catalyst. Generally, the surface area of the catalyst decreases with increasing heating rate velocity.

The maximum calcination temperature also affects the morphological properties of the catalyst. The catalysts become less amorphous, i.e. more crystalline, as the calcination temperature increases. Contrary to many known oxidative dehydrogenation catalysts which require crystallinity to achieve good activity and selectivity, the catalysts compositions of the present invention are active when they are substantially amorphous. Increasing the crystallinity by calcination at increased temperatures above about 700° C. reduces the activity and selectivity of the catalyst of this invention.

The maximum calcination temperature affects the surface area of the catalyst. For example, at a calcination temperature of 850° C. the surface area of the catalyst is about 30 m²/gm and at a calcination temperature of 950° C. the catalyst has a surface area of about 5 m²/gm. Calcination temperatures which result in the formation of oxide catalysts with surface areas of from about 130 m²/gm to about 150 m²/gm are preferred. Catalysts having surface areas deviating from this preferred range of surface areas demonstrate reduced selectivity.

CARRIER

The catalyst may be used with or without a support or carrier. For some applications, a supported catalyst may be preferred. The support may be an inorganic material including, but not limited to, silica, titania, silica-titania, and zirconia. Alumina based supported are not preferred since they contribute to the deactivation or reduced activity of the catalyst. The preferred catalyst support materials are ones which are substantially free of alumina or aluminum.

The support may be loaded with the catalyst to an extent of from about 0 weight percent to about 50 weight percent of the total weight of the support. The catalyst precursor or oxide catalyst is typically deposited on the surface of the support. Alternatively, the catalyst precursor or oxide catalyst may be co-precipitated with a support forming a composition in which the catalyst is substantially uniformly distributed within and on the support. Preferably, the catalyst precursor or oxide catalyst is deposited on the surface of the support and/or the surface of any pores present in the support.

The catalyst precursor, a non-oxidized mixed metal composition, may be formed by co-precipitation in a slurry containing the support to deposit the catalyst precursor directly on the support. The combined catalyst precursor and support may then be calcined to convert the catalyst precursor into the catalytically active oxide form of the catalyst. Alternatively, the catalyst precursor may be prepared and converted to the catalytically active oxide form which may then be deposited on the support by conventional methods, for example by forming a slurry of the oxide catalyst and support followed by filtration or evaporation of the solvent.

PRESSURE

The oxidative dehydrogenation reaction may be conducted at atmospheric or superatmospheric pressures. Generally the reactor pressures will range from about 0.1 Mpa (atmospheric pressure) to about 0.2 MPa (about 2 atmospheres). Preferably the reactor pressure ranges from about 0.1 MPa to about 0.15 MPa.

TEMPERATURE

The temperature for the oxidative dehydrogenation reaction will depend upon the compound being dehydrogenated and the desired level of conversion. The temperature for the oxidative dehydrogenation reaction generally ranges from about 350° C. to about 650° C. A preferred temperature range is from about 350° C. to about 500° C. The catalyst is active at a temperature as low as 300° C. A more preferred temperature range is from about 350° C. to about 450° C. A most preferred temperature range is from about 350° C. to about 400° C. The preferred range for a particular catalyst composition may vary as observed in Tables 2 and 3. For instance, examples 20 and 27 show high selectivity at the relatively low temperature of 450° C. Other examples, such as 16 and 17 show high selectivity at the relatively high temperature of 550° C. The temperatures shown in Tables 2 and 3 are the maximum temperatures in the reactor.

CONTACT TIME

The preferred length of time during which the saturated compound contacts the catalyst is governed by many factors including the reactor temperature, the catalyst composition, and the nature of the compound undergoing reaction. The contact time generally ranges from about 0.1 to about 20 seconds. Contact times of 0.3 to 6 seconds are preferred. Contact times are generally determined empirically to provide an acceptable compromise between conversion of the starting material to product and selectivity in the production of the product.

Percent conversion of starting material=(moles of consumed starting material/moles of starting material fed to the reactor)×100. Percent selectivity for the desired product=(moles of desired product formed/moles of starting material consumed)×100. Percent yield per pass of desired product=(moles of desired product formed/moles of starting material fed to the reactor)×100.

The contact time may be adjusted by co-feeding a diluent, such as nitrogen, carbon dioxide or helium, with the organic compound that will be oxidatively dehydrogenated. The diluent may be any material that is a gas or vapor at the reactor temperature and pressure and which does not react with the organic compound starting material, the unsaturated organic compound product or the catalyst. The diluent may be present in concentrations of up to about 25 moles of diluent per mole of paraffin fed to the reactor. Typically the diluent concentration is from about 7.0 moles to about 10.0 moles per mole of paraffin.

OXYGEN TO OLEFIN RATIO

The amount of oxygen employed in the oxidative dehydrogenation process is determined by factors such as the particular compound being dehydrogenated, the number of hydrogen atoms being removed and the conversion level. Generally oxygen may be supplied to the reaction zone in an amount to provide a paraffin-to-oxygen molar ratio of from about 1/0.01 to about 1/10. Typically the molar ratio of paraffin to oxygen ranges from about 1/0.1 to about 1/1.

The molecular oxygen may be introduced with or without a diluent gas. Suitable diluent gases include, but are not limited to, nitrogen, steam and carbon dioxide. The diluent gas may be added in ratios up to about twenty-five moles of diluent per mole of organic compound feed. The diluent gas is typically used in sufficient quantities to aid in heat removal and to avoid the formation of an explosive gas mixture.

One embodiment according to the present invention is a process for the oxidative dehydrogenation of an organic compound which comprises contacting the compound having at least two adjacent carbon atoms bonded together and each carbon atom having at least one hydrogen atom and having from 2 to 20 carbon atoms in a vapor phase at a temperature of at least about 300° C. in the presence of oxygen with a catalyst comprising $A_aB_bSb_cV_dAl_eO_x$ wherein A is an alkali or alkaline earth metal; B is one or more optional elements selected from zinc, cadmium, lead, nickel, cobalt, iron, chromium, bismuth, gallium, niobium, tin and neodymium; and a is 0 to 0.3, b is 0 to 5, c is 0.5 to 10, d is 1, e is 3 to 10, $7 \leq a+b+c+d+e \leq 25$, and x is determined by the valence requirements of the elements present.

Another embodiment according to the present invention is a process for the oxidative dehydrogenation of an organic compound which comprises contacting the compound having at least two adjacent carbon atoms bonded together and each carbon atom having at least one hydrogen atom and having from 2 to 20 carbon atoms in a vapor phase at a temperature of at least about 300° C. in the presence of oxygen with a catalyst consisting essentially of $A_aB_bSb_cV_dAl_eO_x$ wherein A is an alkali or alkaline earth metal; B is one or more optional elements selected from zinc, cadmium, lead, nickel, cobalt, iron, chromium, bismuth, gallium, niobium, tin and neodymium; and a is 0 to 0.3, b is 0 to 5, c is 0.5 to 10, d is 1, e is 3 to 10, $7 \leq a+b+c+d+e \leq 25$, and x is determined by the valence requirements of the elements present.

REACTOR

The catalyst may be used in either a fixed bed or fluidized bed reactor by using conventional methods to form catalyst particles in the size appropriate for fixed bed or fluidized reactors. The fluidized bed reactor is useful for certain oxidative dehydrogenation reactions, for example propane to propene, which are exothermic. Fluidized bed reactors are sometimes preferred for exothermic reactions since the temperature may be controlled easier than in a fixed bed reactor.

The foregoing disclosure and description of the invention are illustrative and explanatory thereof, and various changes in the details of the illustrated apparatus and construction and method of operation may be made without departing from the spirit of the invention.

EXAMPLE 1

Preparation of Catalyst—$Sb_{0.5}V_{1.0}Al_{6.1}$ 51.5 gm of $Al(NO_3)_3.9H_2O$ was dissolved in 800 mL of deionized water and continuously stirred while 30% $NH_4OH$ was added to adjust the pH to 7.5–8.0 to obtain white flocculent precipitate of alumina. A white slurry of 2.6 gm of $SbCl_3$ in 8 mL of 0.5 N HCl was added to a solution of 2.63 gm of $NH_4VO_3$ dissolved in 75 mL of hot deionized water forming a pale-brown suspension. The pH of the suspension was adjusted to 7.5–8.0 with 30% $NH_4OH$. Under stirring, the slurry obtained was added to that previously prepared alumina slurry to obtain a homogenized mixture. The resulting product was obtained as a cake by filtration. The cake was dried at 120° C. for 5 hours. The cake was calcined by heating from 120° C. to 430° C. at a rate of 20° C./minute and then maintained at 430° C. The heat-up period from 120° C. to 430° C. and the period during which the cake was maintained at 430° C. totaled 4 hours. The temperature was then increased to 650° C. at 20° C./minute. The heat-up period from 430° C. to 650° C. and the period during which the cake was maintained at 650° C. totaled 4.5 hours.

EXAMPLE 2

Preparation of Catalyst—$Ni_{0.3}Sb_{0.5}V_{1.0}Al_{6.1}$ 103.0 gm of $Al(NO_3)_3.9H_2O$ was dissolved in 1600 mL of deionized water and continuously stirred while 30% $NH_4OH$ was added to adjust the pH to 7.5 to obtain a gelatinous precipitate. Separately, 5.26 gm of $NH_4VO_3$ was dissolved in 150 mL of hot deionized water and a solution of 3.4 gm of $NiCl_2.6H_2O$ in 20 mL of deionized $H_2O$ was added to the $NH_4VO_3$ solution to obtain green-orange solution. A white slurry of 5.1 gm of $SbCl_3$ in 15 mL of 0.5 N HCl was added to the $NH_4VO_3$ solution forming a greenish-blue suspension. The pH of the mixture was adjusted by the addition of 30% $NH_4OH$ to 7.5 and metallic gray precipitate was obtained. Under stirring, the resultant slurry was added to that previously prepared alumina slurry to obtain homogenized mixture. The resulting product was obtained as a cake by filtration. The cake was dried at 120° C. for 5 hours. The cake was calcined by heating from 120° C. to 430° C. at a rate of 20° C./minute and then maintained at 430° C. The heat-up period from 120° C. to 430° C. and the period during which the cake was maintained at 430° C. totaled 4 hours. The temperature was then increased to 650° C. at 20° C./minute. The heat-up period from 430° C. to 650° C. and the period during which the cake was maintained at 650° C. totaled 4.5 hours.

EXAMPLE 3

Preparation of Catalyst—$Ni_{0.3}Sb_{1.5}V_{1.0}Al_{6.1}$ 51.5 gm of $Al(NO_3)_3.9H_2O$ was dissolved in 800 mL of deionized water and continuously stirred while 30% $NH_4OH$ was added to adjust the pH to 7.5 to obtain white gelatinous precipitate. Separately, 2.6 gm of $NH_4VO_3$ was dissolved in 75 mL of hot deionized water. A solution of 1.8 gm of $NiCl_2.6H_2O$ in 8 mL of deionized $H_2O$ was added to the $NH_4VO_3$ solution to obtain orange-green suspension. Separately, a white slurry of 7.7 gm of $SbCl_3$ in 20 mL of 0.5 N HCl was added to $NH_4VO_3/NiCl_2$ suspension. The suspension pH was adjusted to 7.5–8.0 with 30% $NH_4OH$ to obtain metallic gray mixture. Under stirring, the resultant slurry was added to that previously prepared alumina slurry to obtain homogenized mixture. The resulting product was obtained as a cake by filtration. The cake was dried at 120° C. for 5 hours. The cake was calcined by heating from 120° C. to 430° C. at a rate of 20° C./minute and then maintained at 430° C. The heat-up period from 120° C. to 430° C. and the period during which the cake was maintained at 430° C. totaled 4 hours. The temperature was then increased to 650° C. at 20° C./minute. The heat-up period from 430° C. to 650° C. and the period during which the cake was maintained at 650° C. totaled 4.5 hours.

EXAMPLE 4

Preparation of Catalyst—$Ni_{0.3}Sb_{3.0}V_{1.0}Al_{6.1}$

The procedure in Example 3 was used except 15.4 gm of $SbCl_3$ in 40 mL of 0.5 N HCl was used.

EXAMPLE 5

Preparation of Catalyst—$Fe_{0.3}Sb_{0.5}V_{1.0}Al_{6.1}$

The procedure in Example 2 was used except 6.1 gm of $Fe(NO_3)_3.9H_2O$ in 15 mL of deionized water was used instead of the nickel salt.

EXAMPLE 6

Preparation of Catalyst—$Fe_{0.3}Sb_{1.5}V_{1.0}Al_{6.1}$

The procedure in Example 2 was used except 3.0 gm of $Fe(NO_3)_3.9H_2O$ was used instead of the nickel salt to produce an olive-green precipitate.

EXAMPLE 7

Preparation of Catalyst—$Fe_{0.3}Sb_{3.0}V_{1.0}Al6.1$

The procedure used in Example 3 was followed except 3.0 gm of $Fe(NO_3)_3.9H_2O$ was used instead of the nickel salt.

EXAMPLES 8–10 and 12–14

Preparation of Catalyst—$M_{0.3}Sb_{0.5}V_{1.0}Al_{6.1}$; where M=Zn, Cd, Co, Bi, Ga, Sn.

The following catalysts were synthesized according to Example 5, except $Fe(NO_3)_3$ was replaced by the metal salts listed in Table 1.

TABLE 1

| Example Number | Metal Salts | Weight in gm. | Solvent (mL) | Final Color of Slurry |
|---|---|---|---|---|
| 8 | $Zn(NO_3)_2.6H_2O$ | 2.23 | Water(15) | Metallic Grey |
| 9 | $Cd(NO_3)_2.4H_2O$ | 2.23 | Water(15) | Grayish Green |
| 10 | $CoCl_2.6H_2O$ | 1.34 | Water(15) | Dark Green |
| 12 | $Bi(NO_3)_3.5H_2O$ | 3.60 | 23% $HNO_3$ (15) | Pale Orange |
| 13 | $Ga(NO_3)_3.2H_2O$ | 2.16 | Water(15) | Metallic Grey |
| 14 | $SnCl_4.5H_2O$ | 2.63 | Water(15) | Metallic Grey |

EXAMPLE 11
Preparation of Catalyst—$Nb_{0.3}Sb_{0.5}V_{1.0}Al_{6.1}$

The procedure in Example 2 was followed except 4.0 gm of $NbCl_3$ dissolved in 15 mL of concentrated HCl was used instead of the nickel salt in water.

EXAMPLE 15
Preparation of Catalyst—$Cr_{0.3}Sb_{0.5}V_{1.0}Al_{6.1}$

The procedure in Example 2 was followed except 6.0 gm of $Cr(NO_3)_3.9H_2O$ was used instead of the nickel salt.

EXAMPLE 16
Preparation of Catalyst—$Nb_{0.16}Fe_{0.17}Sb_{0.5}V_{1.0}Al_{6.1}$ 100.3 gm of $Al(NO_3)_3.9H_2O$ was dissolved in 1600 mL of deionized water and continuously stirred while 30% $NH_4OH$ was added to adjust the pH to 7.5 to obtain a gelatinous precipitate. A solution of 3.0 gm of $Fe(NO_3)_3.9H_2O$ in 20 mL of deionized $H_2O$ was added to a solution of 5.26 gm of $NH_4VO_3$ dissolved in 150 mL of hot deionized water to obtain an orange precipitate. A slurry of 5.1 gm of $SbCl_3$ and a slurry of 2.0 gm of $NbCl_5$, each in 15 mL of 0.5 N HCl, were added to the $NH_4VO_3/Fe(NO_3)_3$ precipitate to form a pale brown suspension. The pH of the mixture was adjusted to 7.5–8.0 with 30% $NH_4OH$. The resultant slurry was added to the previously prepared alumina slurry to obtain a homogenized mixture. The resulting product was obtained as a cake by filtration. The cake was dried at 120° C. for 5 hours. The cake was calcined by heating from 120° C. to 430° C. at a rate of 20° C./minute and then maintained at 430° C. The heat-up period from 120° C. to 430° C. and the period during which the cake was maintained at 430° C. totaled 4 hours. The temperature was then increased to 650° C. at 20° C./minute. The heat-up period from 430° C. to 650° C. and the period during which the cake was maintained at 650° C. totaled 4.5 hours.

EXAMPLE 5
Preparation of Catalyst—$Cr_{0.16}Fe_{0.17}Sb_{0.5}V_{1.0}Al_{6.1}$ The procedure in Example 16 was followed except 6.0 gm of $Cr(No_3)_3.9H_2O$ dissolved in water was used instead of the niobium salt in HCl.

EXAMPLES 18–21
Preparation of Catalyst—$K_xFe_{0.3}Sb_{0.5}V_{1.0}Al_{6.1}$; where x=0.015 (18); 0.03 (19); 0.06 (20); 0.15 (21)

The base material, $Fe_{0.3}Sb_{0.5}V_{1.0}Al_{6.1}$, was prepared by the procedure in Example 5 except that the base material was only calcined at 430° C. for 4.5 hours. Semiconductor grade KOH was dissolved in water and impregnated by incipient wetness onto the base material. The weight of KOH used was calcined according to the atomic ratios indicated in the formulas for each example. The resulting KOH impregnated base material were dried at 120° C. for 5 hours. The product was then heated to 650° C. at a rate of 20° C./minute. The heat-up period from 120° C. to 650° C. and the period during which the product was maintained at 650° C. totaled 4.5 hours.

EXAMPLES 22–25
Preparation of Catalyst—$M_{0.06}Fe_{0.3}Sb_{0.5}V_{1.0}Al_{6.1}$ where M=Na (22); Cs (23); Mg (24); Ba (25)

The procedure in Examples 18–21 was followed sodium hydroxide, cesium hydroxide, magnesium hydroxide, and barium hydroxide were respectively substituted for KOH. The weight of the Na, Cs, Mg and Ba hydroxides used were calculated according to the atomic ratios described in the formulas of Examples 22–25.

EXAMPLES 26–30
Preparation of Catalyst—$M_{0.06}Ni_{0.3}Sb_{0.5}V_{1.0}Al_{6.1}$ where M=Na (26); K (27); Cs (28); Mg (29); Ba (30)

Base material $Ni_{0.3}Sb_{0.5}V_{1.0}Al_{6.1}$ was prepared by the procedure in Example 5 except the base material was only calcined at 430° C. for 4.5 hours. Sodium hydroxide, potassium hydroxide, cesium hydroxide, magnesium hydroxide, and barium hydroxide, respectively, were dissolved in water and impregnated onto the base material by incipient wetness. The weights of the Na, K, Cs, Mg and Ba hydroxides were calculated according to the atomic ratios described in the formulas of Example 26–30, respectively. The resulting metal hydroxide impregnated base material were dried at 120° C. for 5 hours. The product was then heated to 650° C. at a rate of 20° C./minute. The heat-up period from 120° C. to 650° C. and the period during which the product was maintained at 650° C. totaled 4.5 hours.

Catalyst Testing Conditions 0.5 cc of catalyst prepared as described in Examples 1–30 was placed in a ¼ inch I.D. stainless steel fixed bed reactor. Propane, oxygen and helium were fed into the reactor, at the temperatures indicated in Tables 2 and 3, in the volume ratio of 2:1:17. The contact time was 0.3 seconds.

TABLE 2

| Example Number | Catalyst atomic Composition | Temperature (° C.) | Conversion (%) $C_3H_8$ | Conversion (%) $O_2$ | Selectivity to $C_3H_6$ (%) |
|---|---|---|---|---|---|
| 1 | $Sb_{0.5}V_{1.0}Al_{6.1}$ | 350 | 8.8 | 42.3 | 36.9 |
|   |   | 450 | 19.9 | 90.6 | 34.1 |
|   |   | 550 | 47.6 | 100 | 53.6 |
| 2 | $Ni_{0.3}Sb_{0.5}V_{1.0}Al_{6.1}$ | 350 | 6.4 | 43.5 | 45.5 |
|   |   | 450 | 19.2 | 88.4 | 37.3 |
| 3 | $Ni_{0.3}Sb_{1.5}V_{1.0}Al_{6.1}$ | 350 | 11.0 | 35.2 | 47.9 |
|   |   | 450 | 21.6 | 100 | 30.1 |
| 4 | $Ni_{0.3}Sb_{3.0}V_{1.0}Al_{6.1}$ | 350 | 9.4 | 24.7 | 47.5 |
|   |   | 450 | 18.4 | 96.8 | 38.9 |
| 5 | $Fe_{0.3}Sb_{0.5}V_{1.0}Al_{6.1}$ | 350 | 5.3 | 19.8 | 64.3 |
|   |   | 450 | 20.6 | 95.9 | 40.8 |
|   |   | 550 | 40.0 | 100 | 38.3 |
| 6 | $Fe_{0.3}Sb_{1.5}V_{1.0}Al_{6.1}$ | 350 | 10.7 | 40.6 | 40.3 |
|   |   | 450 | 17.8 | 97.5 | 36.3 |
| 7 | $Fe_{0.3}Sb_{3.0}V_{1.0}Al_{6.1}$ | 350 | 1.9 | 36.3 | 30.7 |
|   |   | 450 | 15.8 | 100 | 34.6 |
| 8 | $Zn_{0.3}Sb_{0.5}V_{1.0}Al_{6.1}$ | 350 | 5.2 | 25.7 | 55.6 |
|   |   | 450 | 20.7 | 97.3 | 39.7 |
|   |   | 550 | 41.5 | 100 | 49.4 |
| 9 | $Cd_{0.3}Sb_{0.5}V_{1.0}Al_{6.1}$ | 350 | 3.7 | 28.3 | 46.4 |
|   |   | 450 | 18 | 99.4 | 24.9 |
|   |   | 550 | 33.7 | 100 | 36.9 |
| 10 | $Co_{0.3}Sb_{0.5}V_{1.0}Al_{6.1}$ | 350 | 6.0 | 24.5 | 46.4 |
|   |   | 450 | 19.1 | 99.5 | 31.3 |
|   |   | 550 | 33.4 | 100 | 46.4 |
| 11 | $Nb_{0.3}Sb_{0.5}V_{1.0}Al_{6.1}$ | 450 | 18.3 | 100 | 34.5 |
|   |   | 550 | 46.3 | 100 | 55.4 |
| 12 | $Bi_{0.3}Sb_{0.5}V_{1.0}Al_{6.1}$ | 350 | 4.0 | 11.1 | 61.8 |
|   |   | 450 | 15.9 | 89.5 | 46.5 |
|   |   | 550 | 24.0 | 100 | 42.7 |
| 13 | $Ga_{0.3}Sb_{0.5}V_{1.0}Al_{6.1}$ | 350 | 9.7 | 45.9 | 38.5 |
|   |   | 450 | 18.5 | 90.7 | 35.8 |
|   |   | 550 | 47.1 | 100 | 52.4 |
| 14 | $Sn_{0.3}Sb_{0.5}V_{1.0}Al_{6.1}$ | 350 | 14.6 | 65.8 | 32.9 |
|   |   | 450 | 18.8 | 100 | 37.0 |
| 15 | $Cr_{0.3}Sb_{0.5}V_{1.0}Al_{6.1}$ | 350 | 19.7 | 85.8 | 35.0 |
|   |   | 450 | 29.3 | 100 | 38.3 |
|   |   | 550 | 37.4 | 100 | 45.8 |
| 16 | $Nb_{0.16}Fe_{0.17}Sb_{0.5}V_{1.0}Al_{6.1}$ | 450 | 18.2 | 100 | 41.6 |
|   |   | 550 | 34.5 | 100 | 54.8 |
| 17 | $Cr_{0.16}Fe_{0.17}Sb_{0.5}V_{1.0}Al_{6.1}$ | 450 | 19.7 | 100 | 38.8 |
|   |   | 550 | 35.8 | 100 | 52.6 |

TABLE

| Example Number | Catalyst atomic Composition | Temperature (° C.) | Conversion (%) $C_3H_8$ | Conversion (%) $O_2$ | Selectivity to $C_3H_6$ (%) |
|---|---|---|---|---|---|
| 18 | $K_{0.15}Fe_{0.3}Sb_{0.5}V_{1.0}Al_{6.1}$ | 350 | 3.5 | 15.0 | 65.3 |
|  |  | 400 | 12.0 | 64.4 | 46.1 |
|  |  | 450 | 20.0 | 100 | 45.2 |
| 19 | $K_{0.3}Fe_{0.3}Sb_{0.5}V_{1.0}Al_{6.1}$ | 350 | 3.1 | 8.6 | 75.0 |
|  |  | 400 | 10.2 | 39.8 | 56.2 |
|  |  | 450 | 20.9 | 100 | 47.0 |
| 20 | $K_{0.06}Fe_{0.3}Sb_{0.5}V_{1.0}Al_{6.1}$ | 350 | 2.1 | 5.8 | 85.7 |
|  |  | 450 | 15.5 | 51.3 | 56.2 |
|  |  | 550 | 23.7 | 100 | 42.9 |
| 21 | $K_{0.15}Fe_{0.3}Sb_{0.5}V_{1.0}Al_{6.1}$ | 400 | 2.7 | 15.9 | 75.0 |
|  |  | 450 | 5.5 | 30.9 | 66.7 |
| 22 | $Na_{0.06}Fe_{0.3}Sb_{0.5}V_{1.0}Al_{6.1}$ | 350 | 8.6 | 47.1 | 43.3 |
|  |  | 450 | 18.6 | 97.5 | 38.9 |
|  |  | 550 | 32.6 | 100 | 54.3 |
| 23 | $Cs_{0.06}Fe_{0.3}Sb_{0.5}V_{1.0}Al_{6.1}$ | 350 | 11.8 | 24.3 | 58.6 |
|  |  | 450 | 24.0 | 100 | 41.3 |
| 24 | $Mg_{0.06}Fe_{0.3}Sb_{0.5}V_{1.0}Al_{6.1}$ | 350 | 15.8 | 48.9 | 35.5 |
|  |  | 450 | 26.4 | 100 | 27.8 |
|  |  | 550 | 33.8 | 100 | 45.3 |
| 25 | $Ba_{0.06}Fe_{0.3}Sb_{0.5}V_{1.0}Al_{6.1}$ | 350 | 15.4 | 45.3 | 39.1 |
|  |  | 450 | 20.8 | 98.3 | 36.0 |
|  |  | 550 | 25.3 | 100 | 40.0 |
| 26 | $Na_{0.06}Ni_{0.3}Sb_{0.5}V_{1.0}Al_{6.1}$ | 350 | 10.3 | 26.9 | 55.7 |
|  |  | 450 | 22.3 | 100 | 41.5 |
| 27 | $K_{0.06}Ni_{0.3}Sb_{0.5}V_{1.0}Al_{6.1}$ | 350 | 2.2 | 5.1 | 88.1 |
|  |  | 450 | 11.9 | 51.3 | 62.1 |
|  |  | 550 | 32.3 | 100 | 49.0 |
| 28 | $Cs_{0.06}Ni_{0.3}Sb_{0.5}V_{1.0}Al_{6.1}$ | 350 | 9.2 | 26.7 | 57.5 |
|  |  | 400 | 22.3 | 100 | 56.8 |
|  |  | 550 | 35.0 | 100 | 55.5 |
| 29 | $Mg_{0.06}Ni_{0.3}Sb_{0.5}V_{1.0}Al_{6.1}$ | 350 | 11.2 | 30.1 | 51.4 |
|  |  | 450 | 20.7 | 100 | 39.2 |
|  |  | 550 | 34.6 | 100 | 55.0 |
| 30 | $Ba_{0.06}Ni_{0.3}Sb_{0.5}V_{1.0}Al_{6.1}$ | 350 | 4.3 | 33.5 | 60.1 |
|  |  | 450 | 19.3 | 93.6 | 56.8 |
|  |  | 550 | 32.7 | 100 | 54.9 |

What is claimed is:

1. A catalyst composition for the oxidative dehydrogenation of a compound having at least two adjacent carbons atoms bonded to one another and each carbon atom having at least one hydrogen atom bonded thereto comprising $$A_aB_bSb_cV_dAl_eO_x$$

wherein A is an alkali or alkaline earth metal; B is one or more optional elements selected from zinc, cadmium, lead, nickel, cobalt, iron, chromium, bismuth, gallium, niobium, tin and neodymium; and a is 0 to 0.3, b is 0 to 5, c is 0.5 to 10, d is 1, e is 3 to 10, $7 \leq a+b+c+d+e \leq 25$, and x is determined by the valence requirements of the elements present and wherein the catalyst composition is of an amorphous structure.

2. The catalyst of claim 1, having a surface area of from about 130 to about 150 meters squared per gram.

3. A The catalyst of claim 1, wherein the catalyst was produced at a calcination temperature of from about 450° C. to about 650° C.

4. The catalyst of claim 3, wherein to reach the calcination temperature an elevating temperature velocity of about 20° C. per minute was utilized.

5. The catalyst of claim 1, wherein the catalyst composition is on a support.

6. The catalyst of claim 5, wherein the support contains substantially no aluminum.

7. The catalyst of claim 6, wherein the support is silica, titania or zirconia.

8. The catalyst of claim 1, wherein a is from about 0.01 to about 0.1; b is from about 0.1 to about 1; c is from about 0.5 to about 3; e is from about 4 to about 7; and x is determined by the valence of the elements present.

9. The catalyst of claim 1, wherein A is at least one of the elements selected from the group consisting of potassium, cesium, magnesium and barium and wherein B is at least one of the elements selected from the group consisting of zinc, nickel, cobalt, iron, bismuth and niobium.

\* \* \* \* \*